US00PP23148P2

(12) United States Plant Patent
Gilford et al.

(10) Patent No.: US PP23,148 P2
(45) Date of Patent: Oct. 30, 2012

(54) STRAWBERRY PLANT NAMED 'DRISSTRAWNINETEEN'

(50) Latin Name: *Fragaria×ananassa*
Varietal Denomination: DrisStrawNineteen

(75) Inventors: Kristie L. Gilford, Dover, FL (US); Jorge Rodriguez Alcazar, Texcoco (MX); Bruce D. Mowrey, Watsonville, CA (US); Philip J. Stewart, Watsonville, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 13/135,610

(22) Filed: Jul. 11, 2011

(51) Int. Cl.
*A01H 5/00* (2006.01)

(52) U.S. Cl. ..... Plt./209

(58) Field of Classification Search ..... Plt./209
See application file for complete search history.

*Primary Examiner* — Annette Para
(74) *Attorney, Agent, or Firm* — Jondle & Associates, P.C.

(57) ABSTRACT

A new and distinct variety of strawberry plant named 'DrisStrawNineteen' characterized by having medium sized, conical to bi-conical shaped berries that are medium red in color, and having a medium to strong sweetness, is disclosed.

3 Drawing Sheets

Genus and species: *Fragaria×ananassa.*
Variety denomination: 'DrisStrawNineteen'.

BACKGROUND OF THE NEW PLANT

The present invention relates to a new and distinct strawberry variety designated 'DrisStrawNineteen' and botanically known as *Fragaria×ananassa*. This new strawberry variety was the result of a controlled cross conducted in Hillsborough, Fla. in 2004 between the proprietary female parent 'Driscoll Atlantis' (U.S. Plant Pat. No. 16,475) and the proprietary male parent '43J313' (unpatented). A single plant was selected for asexual propagation via tissue culture and vegetative cuttings in Shasta County, Calif. in 2005.

'DrisStrawNineteen' underwent further testing in Hillsborough, Fla. for seven years (2004-2011). The present invention has been found to retain its distinctive characteristics through several asexual propagations via stolons.

Plant Breeder's Rights for this variety have not been applied for. 'DrisStrawNineteen' has not been made publicly available or sold more than one year prior to the filing date of this application.

DESCRIPTION OF THE PHOTOGRAPHS

The accompanying color photographs show typical specimens of the new variety at various stages of development. The colors shown are as true as can be reasonably obtained by conventional photographic procedures. The photographs were taken from four-month-old plants.

DESCRIPTION OF THE NEW VARIETY

Figure 1:
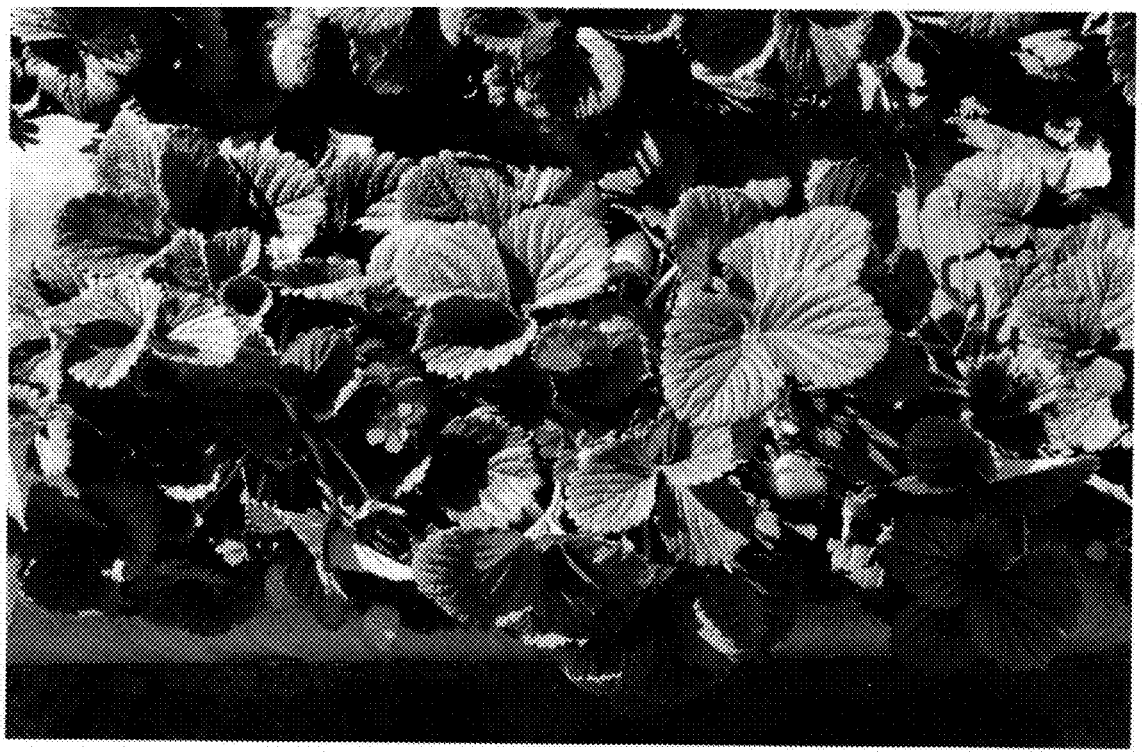
FIG. 1 shows overall plant habit including fruit at various stages of development.
Figure 2:
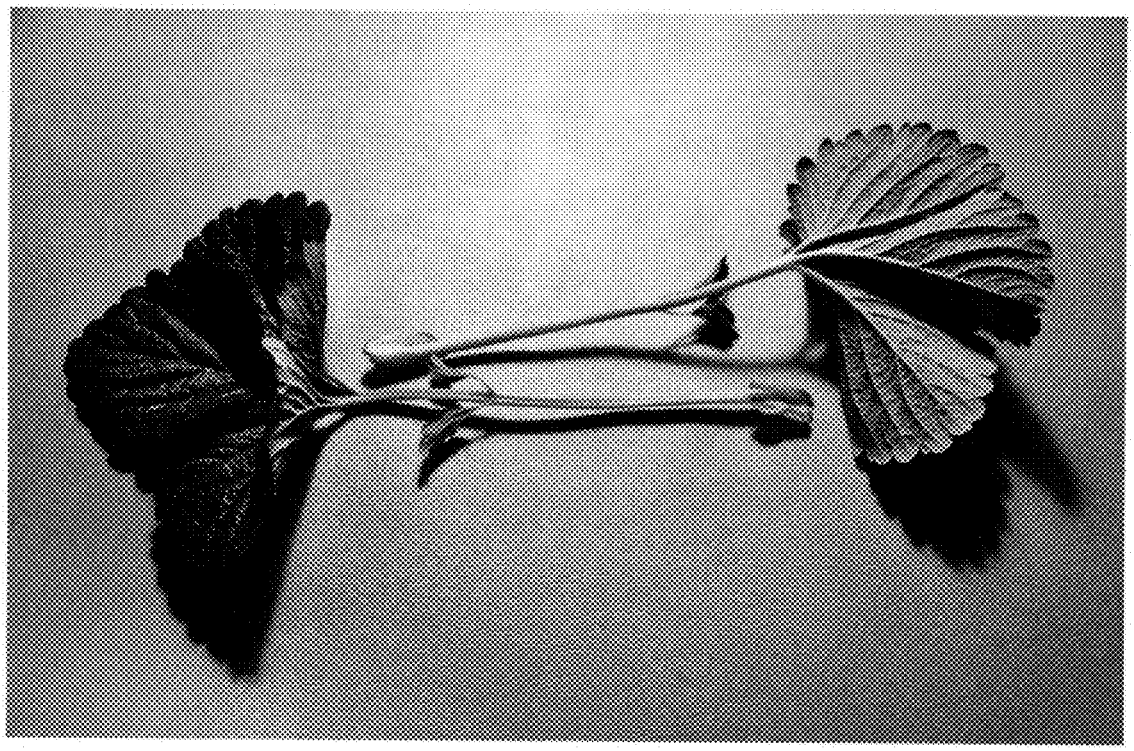
FIG. 2 shows leaves of the plant with three leaflets.
Figure 3:
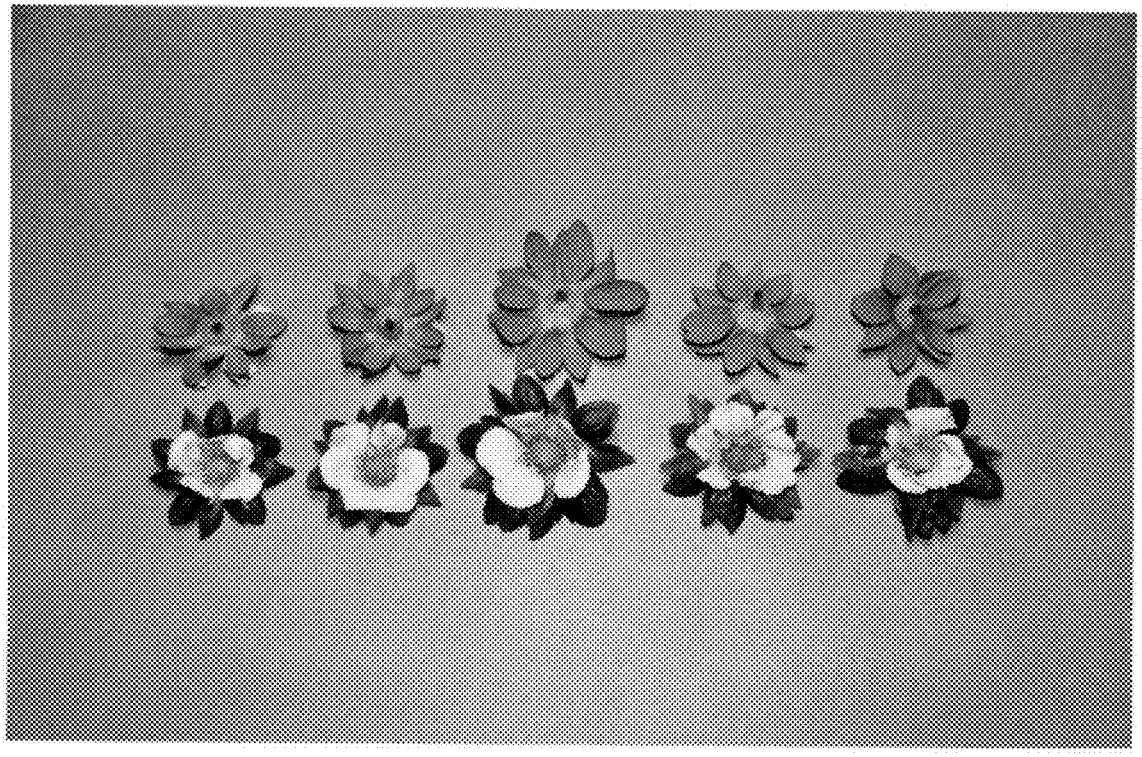
FIG. 3 shows both upper and lower surfaces of the flowers.
Figure 4:
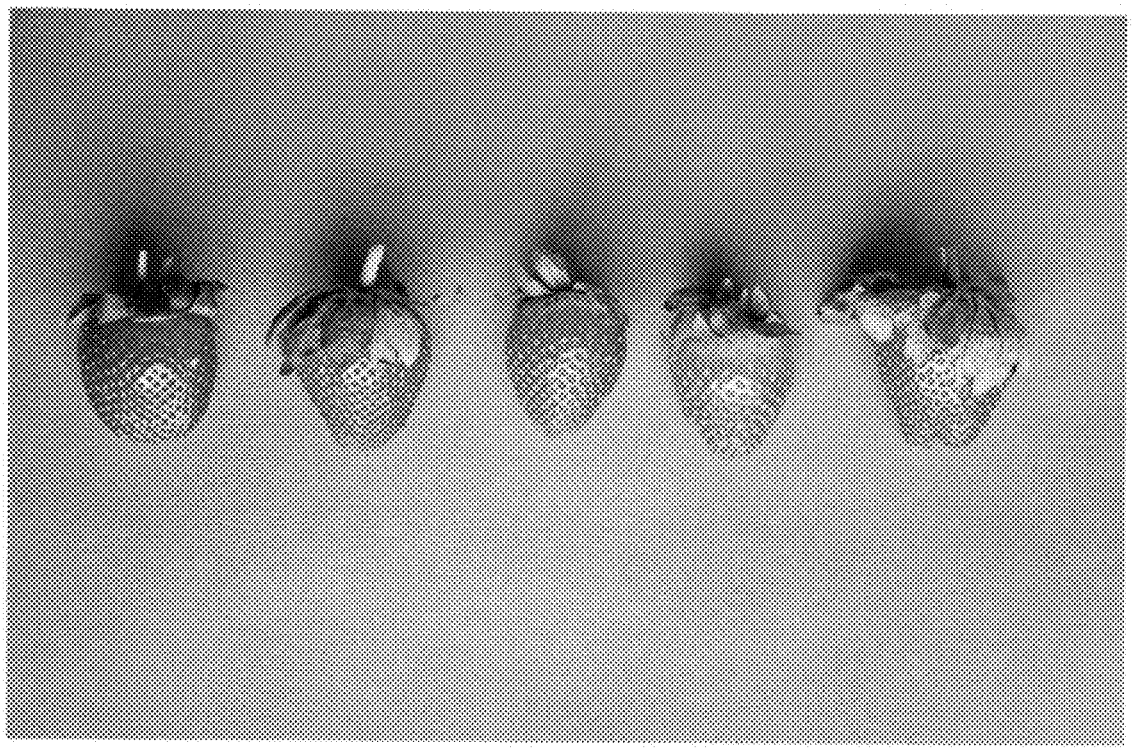
FIG. 4 shows the whole fruit.
Figure 5:
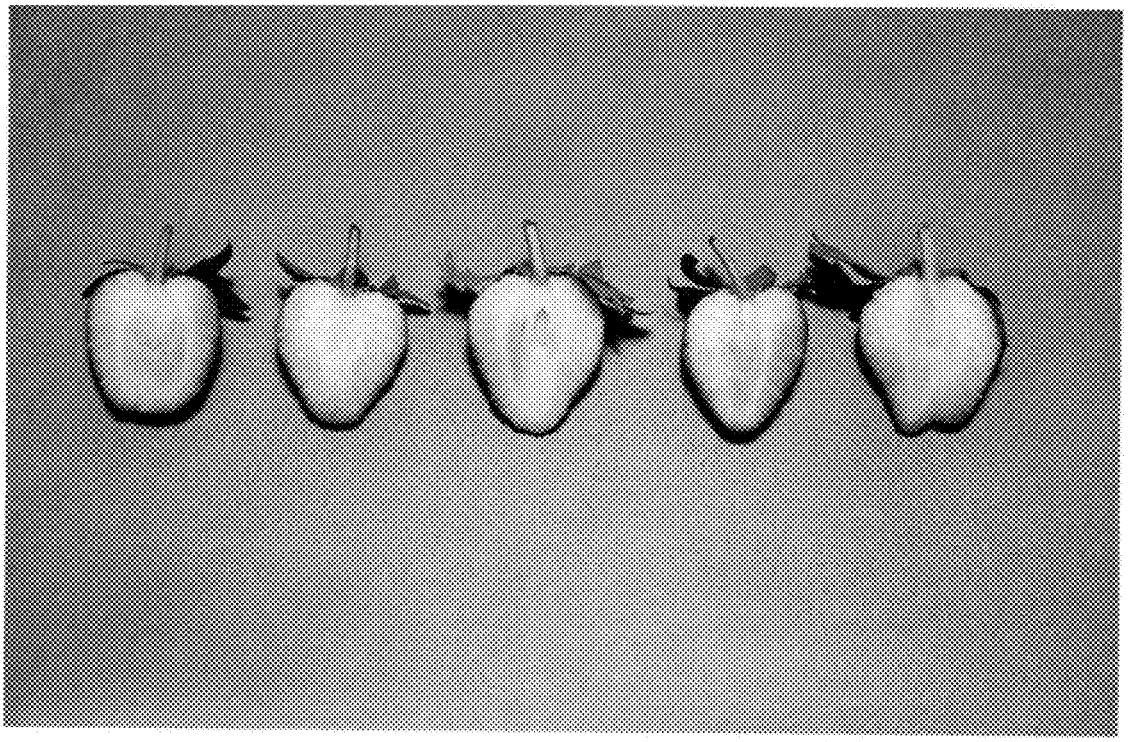
FIG. 5 shows the fruit in longitudinal cross-section.

The following detailed descriptions set forth the distinctive characteristics of 'DrisStrawNineteen'. The data which define these characteristics is based on observations taken in Hillsborough, Fla. from 2004 to 2011. This description is in accordance with UPOV terminology. Color designations, color descriptions, and other phenotypical descriptions may deviate from the stated values and descriptions depending upon variation in environmental, seasonal, climatic, and cultural conditions. 'DrisStrawNineteen' has not been observed under all possible environmental conditions. The botanical description of 'DrisStrawNineteen' was taken from four-month-old plants. Color terminology follows The Royal Horticultural Society Colour Chart, London (R.H.S.) (2001).

DETAILED BOTANICAL DESCRIPTION OF THE PLANT

Classification:
- *Species.*—*Fragaria×ananassa.*
- *Common name.*—Strawberry.
- *Denomination.*—'DrisStrawNineteen'.

Parentage:
- *Female parent.*—The proprietary variety 'Driscoll Atlantis' (U.S. Plant Pat. No. 16,475).
- *Male parent.*—The proprietary variety '43J313' (unpatented).

Plant:
- *Height.*—23.0 cm.
- *Diameter.*—44.7 cm.
- *Number of crowns/plant.*—3.
- *Habit.*—Flat globose.
- *Density of individual plant.*—Medium.
- *Vigor.*—Medium.

Leaves:
- *Terminal leaflet length.*—9.1 mm.
- *Terminal leaflet width.*—8.6 mm.
- *Terminal leaflet length/width ratio.*—1.1.
- *Number of teeth/terminal leaflet.*—23.
- *Shape of teeth.*—Rounded-crenate.
- *Color.*—Upper surface: Dark; RHS 137A (Dark green). Lower surface: Medium; RHS 138B (Medium green).
- *Leaf shape in cross section.*—Concave.

*Leaf blistering*.—Medium.
*Leaf glossiness*.—Medium.
*Number of leaflets*.—3 only.
*Terminal leaflet margin profile*.—Revolute (margins rolled backwards).
*Terminal leaflet length/width ratio*.—As long as broad (1:1).
*Terminal leaflet shape*.—Orbicular.
*Terminal leaflet base shape*.—Rounded.
*Terminal leaflet apex descriptor*.—Convex.
*Terminal leaflet size*.—Medium.
*Terminal leaflet variegation*.—Absent.
*Terminal leaflet margin*.—Crenate.

Petiole:
*Length*.—Long; 14.2 cm.
*Diameter*.—4.23 mm.
*Pubescence*.—Dense.
*Pose of hairs*.—Upwards.
*Color*.—RHS 145A (Medium Yellow-green).

Petiolule:
*Color*.—RHS 145A (Medium Yellow-green).
*Length*.—13.74 mm.
*Diameter*.—2.00 mm.
*Bract frequency*.—1.

Stipule:
*Length*.—3.5 cm.
*Width*.—7.85 mm.
*Pubescence*.—Medium.
*Stipule anthocyanin coloration*.—Absent or very weak.
*Stipule anthocyanin color*.—RHS 145C (Light yellow-green).

Stolon:
*Number*.—Many.
*Average number of daughter plants per plant*.—78.
*Stolon anthocyanin*.—Absent or very weak.
*Stolon anthocyanin color*.—RHS 70B Medium red-purple.
*Thickness*.—Medium.
*Pubescence*.—Dense.

Inflorescence:
*Position relative to foliage*.—Beneath.
*Number of flowers*.—Medium.
*Time of flowering* (50% *of plants at first flower*).—Very early.
*Flower size*.—Medium.
*Diameter*.—29.96 mm; Medium.
*Petals*.—Shape: Orbicular. Apex: Rounded. Base: Concave-convex. Margin: Entire. Spacing: Free to touching to overlapping. Length: 14.73 mm. Width: 14.02 mm. Length/width ratio: 1.1 As long as broad. Typical and observed petal number per flower: 6. Color (upper surface): RHS 155C (White).
*Calyx*.—Diameter: 41.28 mm. Diameter relative to corolla: Larger. Inner calyx diameter relative to outer: Same size.
*Sepal*.—Shape: Elliptical and obovate. Apex: Convex. Margin: Entire. Length: 15.49 mm. Width: 8.73 mm. Typical and observed sepal number per flower: 12. Receptacle color: RHS N144D (Medium yellow-green). Anther color: RHS 163B (Medium greyed-orange). Stamen: Present.
*Pedicel*.—Attitude of hairs: Upwards.

Fruiting truss:
*Length*.—Medium: 12.7 cm.
*Diameter at base of truss*.—3.57 mm.
*Number of berries per fruiting truss*.—1.
*Attitude at first picking*.—Prostrate.
*Color at base of truss*.—RHS 146D (Medium yellow-green).

Fruit:
*Length*.—46.17 mm.
*Width*.—37.67 mm.
*Length/width ratio*.—1.2.
*Fruit hollow length*.—15.12 mm.
*Fruit hollow width*.—8.09 mm.
*Fruit hollow length/width ration*.—1.9.
*Fruit hollow center* (*cavity*).—Small.
*Weight* (*per individual berry*).—25.3 g.
*Fruit ratio of length/maximum width*.—As long as broad.
*Relative fruit size*.—Medium.
*Predominant fruit shape*.—Conical to bi-conical.
*Difference in shape between primary and secondary fruits*.—Slight.
*Unevenness of fruit surface*.—Even or very slightly uneven.
*Fruit skin color*.—RHS 46A (Dark red).
*Evenness of fruit color*.—Even or very slightly uneven.
*Fruit glossiness*.—Medium.
*Insertion of achenes*.—Above surface.
*Achene coloration* (*sunward side of berry*).—RHS N144B (Medium yellow-green).
*Achene coloration* (*shaded side of berry*).—RHS 145B (Medium yellow-green).
*Achenes per berry*.—247.
*Achene weight* (*weight achenes divided by total # seed*).—0.000598463.
*Band without achenes*.—Broad.
*Insertion of calyx*.—Set above fruit — raised.
*Pose of calyx segments*.—Clasping the fruit — downwards to reflexed — upwards.
*Size of calyx in relation to fruit*.—Much larger.
*Adherence of calyx*.—Strong.
*Firmness of flesh*.—Firm.
*Color of flesh* (*excluding core*).—Whitish and medium red. RHS 155B (White) and RHS 41B (Medium-red).
*Color of core*.—RHS 155B (White).
*Evenness of flesh color*.—Uneven.
*Distribution of flesh color*.—Marginal and central.
*Sweetness*.—Medium to strong.
*Acidity*.—Weak.
*Texture when tasted*.—Medium.
*Type of bearing*.—Day neutral.
*Grams of fruit/plant*.—210.
*Harvest interval*.—Early October to late March.
*Harvest maturity*.—Very early.

Disease, pest, and stress resistance:
*Botrytis fruit rot*.—Moderately resistant.
*Powdery mildew*.—Moderately resistant.
*Xanthomonas fragariae*.—Moderately resistant.
*Tetranychus urticae*.—Moderately resistant.
*Lygus hesperus* (*Lygus bug*).—Highly susceptible.

COMPARISON WITH PARENTAL AND COMMERCIAL VARIETIES

When 'DrisStrawNineteen' is compared to the proprietary female parent 'Driscoll Atlantis' (U.S. Plant Pat. No. 16,475), 'DrisStrawNineteen' is an upright and moderately open plant, whereas 'Driscoll Atlantis' is a flat-globose and medium to dense plant. 'DrisStrawNineteen' is moderately resistant to *Tetranychus urticae*, Botrytis fruit rot and Powdery Mildew, while 'Driscoll Atlantis' is susceptible to *Tetranychus urticae*, Botrytis Fruit Rot and Powdery Mildew. The fruit band without achenes is broad for 'DrisStrawNineteen', while 'Driscoll Atlantis' has a very narrow fruit band. Additionally, 'DrisStrawNineteen' has smaller fruit and a lower yield than 'Driscoll Atlantis'.

When 'DrisStrawNineteen' is compared to the proprietary male parent '43J313' (unpatented), 'DrisStrawNineteen' has a higher yield and larger fruit than '43J313'.

When 'DrisStrawNineteen' is compared to the commercial variety 'Driscoll Osceola' (U.S. Plant Pat. No. 15,752), 'DrisStrawNineteen' has a conical to bi-conical shape, weak acidity, firm flesh, and a medium to strong sweetness, while 'Driscoll Osceola' has a cordate shaped fruit, medium acidity, soft to medium flesh and a medium sweetness. In addition, 'DrisStrawNineteen' is moderately resistant to *Tetranychus urticae*, Botrytis fruit rot and Powdery Mildew, while 'Driscoll Osceola' is susceptible to *Tetranychus urticae*, and Botrytis fruit rot and moderately susceptible to Powdery Mildew.

We claim:

1. A new and distinct variety of strawberry plant as described and shown herein.

* * * * *